United States Patent [19]

Sasaki et al.

[11] 4,436,656

[45] Mar. 13, 1984

[54] NOVEL ANTITUMOR GLYCOPROTEIN SUBSTANCE AND ITS PREPARATION

[75] Inventors: Takuma Sasaki, Tokyo; Kazuya Nakamichi; Yakudo Tachibana, both of Sohka; Kiyoshi Minami, Koshigaya, all of Japan

[73] Assignee: Maruzen Oil Co., Ltd., Osaka, Japan

[21] Appl. No.: 519,724

[22] Filed: Aug. 2, 1983

[30] Foreign Application Priority Data

Aug. 9, 1982 [JP] Japan ................................ 57-137209

[51] Int. Cl.³ ............................ A23J 1/04; C07G 7/00
[52] U.S. Cl. ................................... 260/112 R; 424/95; 424/177
[58] Field of Search .................................. 260/112 R

[56] References Cited

U.S. PATENT DOCUMENTS

| 3,862,122 | 1/1975 | Peniston et al. ............ 260/112 R X |
| 4,199,496 | 4/1980 | Peniston et al. ................ 260/112 R |
| 4,390,468 | 6/1983 | Sasaki et al. .................... 260/112 R |

OTHER PUBLICATIONS

J. of National Cancer Institute, vol. 60, No. 6, pp. 1499–1500, Jun., 1978, Sasaki et al.

*Primary Examiner*—Howard E. Schain
*Attorney, Agent, or Firm*—Larson and Taylor

[57] ABSTRACT

A novel glycoprotein substance possessing a high antitumor activity is provided, which is recovered and isolated from the liquid portion coming from cooking of raw scallop shellfish with a hot aqueous solvent or vapor of such solvent and which is amphoteric electrolyte in nature with an average molecular weight of about 5000 and with an isoelectric point of pH 5.2.

4 Claims, 2 Drawing Figures

NOVEL ANTITUMOR GLYCOPROTEIN SUBSTANCE AND ITS PREPARATION

FIELD OF THE INVENTION

This invention relates to a novel antitumor glycoprotein substance and a process for the preparation thereof from scallop shellfish.

BACKGROUND OF THE INVENTION

We have already found and reported that several antitumor substances are obtained from meat portion of shellfish and exhibit wide antitumor spectra with little or no cytotoxicity (refer to Japanese Patent Publication No. 8088/82 and Japanese Patent KOKAI Nos. 41314/79 and 41315/79). To be concrete, the first substance we found is a water-soluble, thermally stable glycoprotein having a molecular weight range within the limits of 100,000 and 300,000 (Japanese Patent Publication No. 8088/82). Japanese Patent KOKAI No. 41314/79 describes four substances all of which are water-soluble glycoprotein substances having an average molecular weight of about 20,000 and an isoelectric point of pH 4.5 with somewhat different physical properties from one another and are extracted from meat portion of scallop from which the liver has been removed. Japanese Patent KOKAI No. 41315/79 provides a water-soluble glycoprotein substance having an average molecular weight of 10,000~30,000 which is obtained from meat portion of shellfish, particularly of scallop, wreath shell, tokobushi (Haliotis japonica) and pearl-oyster, from which the liver has been removed.

After that, we have further found that the liquid portion which comes from cooking of raw shellfish with a hot aqueous solvent or with the vapor of such solvent for taking up edible portions thereof and which is to be discarded as waste can also serve as raw material from which water-soluble, macromolecular glycoprotein substances similar to those already obtained from shellfish as above-mentioned are recovered and that these substances have a range of molecular weights within the limits of from 10,000 to 300,000 and possess a significant antitumor activity (refer to T. Sasaki et al, U.S. patent application Ser. No. 404,971, now U.S. Pat. No. 4,390,468).

Thus, the known antitumor substances derived from shellfish may be divided into two broad classes, namely water-soluble glycoproteins having a molecular weight range within the limits of 10,000 and 30,000, typically of around 20,000, and those having a molecular weight range within the limits of 100,000 and 300,000.

We have continued our investigations on antitumor substances derived from mollusc, particularly from shellfish, with the intention of obtaining novel antitumor substances which possess wide antitumor spectra with low cytotoxicities and which exhibit high antitumor activities particularly against solid tumors which are known to be difficult in clinical treatment thereof and discovered such phenomenon on a dry powder derived from the liquid portion to be discarded as waste which comes from the cooking of raw scallop in an aqueous solvent such as water or a saline solution or with vapor of such solvent as being inexplainable from the nature and properties of known antitumor substances of the same origin already reported. On the basis of this discovery, we have followed up our study thereon and successfully isolated a new antitumor substance of a relatively low molecular weight from the dry powder.

Among so-called chemotherapeutic agents, one of the most interesting classes is antitumor substances possessing immunostimulating or immunopotentiating activities. Since, however, known antitumor substances are of relatively high molecular weight, in general, there is a fear of anaphylaxis to occur due to antigen-antibody reaction resulting from the administration of such a high molecular weight substance. In contrast, the antitumor substance according to this invention is of relatively low molecular weight which thus seems to have little such a fear, so that it is expected and interested to be of high value as antitumor agent.

SUMMARY OF THE INVENTION

Accordingly, it is the main object of this invention to provide a novel glycoprotein substance possessing a significant antitumor activity. Another object of this invention is to provide a process for the preparation of the novel glycoprotein substance from the liquid portion, i.e. waste liquor, coming from cooking of raw scallop shellfish. A further object of this invention is to provide an antitumor agent with a low toxicity. These and other objects of this invention will become clear from the following descriptions.

According to the first aspect of this invention, therefore, there is provided a glycoprotein substance possessing an antitumor activity which is recovered from the liquid portion which comes from cooking of raw scallop with a hot aqueous solvent or with the vapor of such solvent and which has the following characteristics:

(1) Appearance: White, powdery solid.
(2) Solubility: Soluble in water, but insoluble in organic solvents such as methanol, ethanol and acetone.
(3) Acidic or basic nature: Amphoteric electrolyte having an isoelectric point of pH 5.2.
(4) Infrared absorption spectrum (pelleted in KBr): With characteristic absorption peaks at 3500~3300, 1660 and 1550 cm$^{-1}$.
(5) Ultraviolet absorption spectrum in an aqueous solution: With a characteristic absorption peak $\lambda_{max}^{H2O}$ at 279 nm.
(6) Color reactions: Positive in biuret reaction, xanthoproteic reaction, phenolic reagent reaction according to Lowry-Folin method, anthrone-sulfuric acid reaction and phenol-sulfuric acid reaction; but negative in cysteine-sulfuric acid reaction.
(7) Average molecular weight: About 5000 as measured by gel-electrophoresis.

DETAILED DESCRIPTION OF THE INVENTION

The novel glycoprotein substance according to this invention is derived from natural sources, particularly from the liquid portion coming from the cooking of raw scallop in an aqueous solvent or with vapor of such solvent, and is a homogeneous substance of relatively low molecular weight which shows a single peak in liquid chromatography and in gel-filtration chromatography and shows a single band in electrophoresis such as disc gel-electrophoresis, which corresponds to powder F obtained in Example 3 hereinafter given. This substance has the following physico-chemical properties:

(1) Elementary analysis: C 43.8; H 7.2; N 13.2; S 0.05; P 0.02; Ash 1.0% by weight.

(2) Molecular weight: About 5000 daltons as average molecular weight obtained by SDS-5% and 20% polyacrylamide gel-electrophoresis using as standard substances insulin, cytochrome C, myoglobin, chymotrypsinogen A, tryptophane and ovalbumin wherein comparison is made between Rf value (relative mobility) of the sample and those values of the standard substances to estimate the molecular weight of the former correlatively.

(3) Rf value (relative mobility) in electrophoresis: A single peak band at Rf value of 0.94 relative to that of Bromophenol blue as standard in electrophoresis on 20% acrylamide gel at pH 8.0.

(4) Melting point: No definite melting point and no definite decomposition point are seen, but some decomposition is observed at 240° C.

Figure 2:
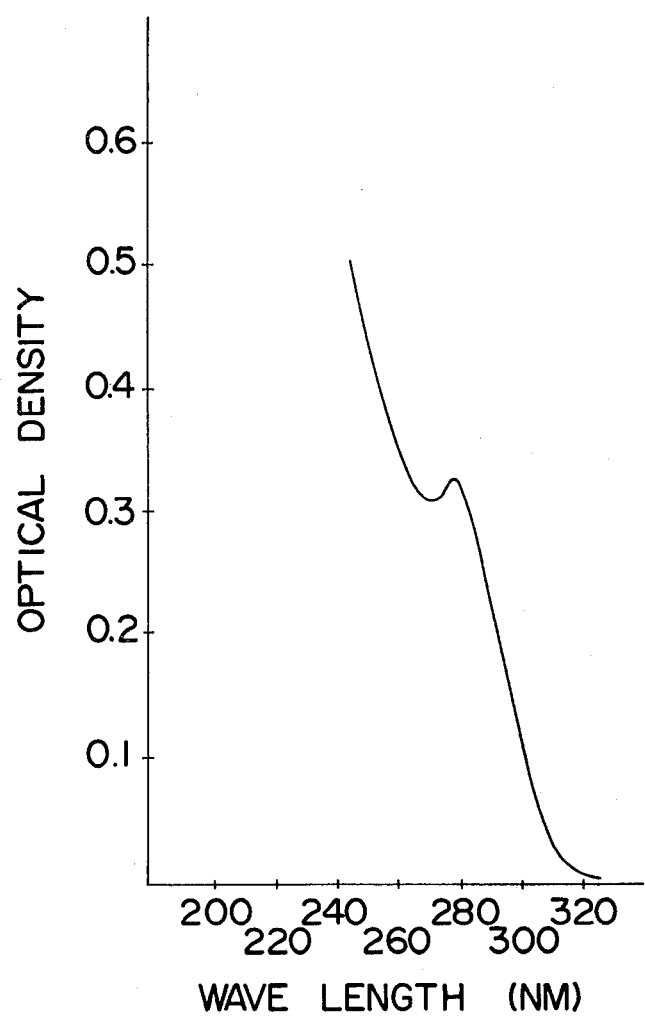

(5) Ultraviolet absorption spectrum: An aqueous solution of the sample reveals the UV absorption spectrum as shown in FIG. 2 with a characteristic absorption peak $\lambda_{max}^{H2O}$ at 279 nm.

Figure 1:
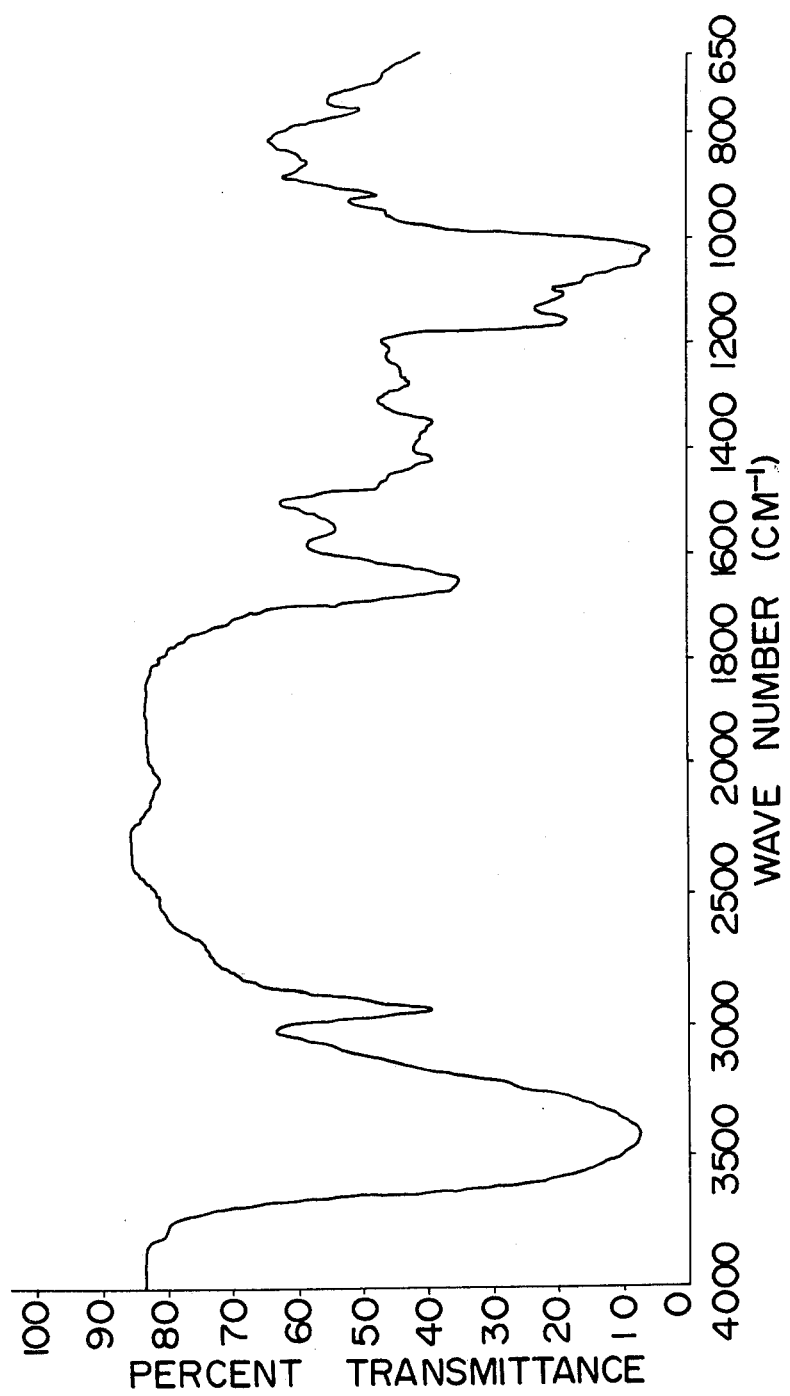
FIG. 1 shows infrared absorption spectrum of a sample of glycoprotein substance according to this invention (powder (F) obtained in Example 3 hereinafter given) pelleted in KBr and FIG. 2 shows ultraviolet absorption spectrum of the same sample in the form of a 0.3 mg/ml aqueous solution.

(6) Infrared absorption spectrum (pelleted in KBr): As shown in FIG. 1 with characteristic absorption peaks at 3500~3300, 2940, 1660, 1550 and 1420 $cm^{-1}$.

(7) Color reactions: Positive in biuret reaction, xanthoproteic reaction, phenolic reagent reaction according to Lowry-Folin method, anthrone-sulfuric acid reaction and phenol-sulfuric acid reaction, but negative in cysteine-sulfuric acid reaction.

(8) Acidic or basic nature: Amphoteric electrolyte having an isoelectric point of pH 5.2.

(9) Solubility: Soluble in water, but insoluble in organic solvents such as methanol, ethanol and acetone.

(10) Appearance: White, powdery solid.

(11) Carbohydrate content: 17.2% by weight calculated in terms of glucose when measured by the phenol-sulfuric acid method.

(12) Amino acids in hydrolyzate: When hydrolyzed in 6N HCl at 105~110° C. for 24 hours, the resulting hydrolyzate contains at least the following amino acids: aspartic acid, threonine, serine, glutamic acid, glycine, alanine, valine, isoleucine, leucine, tyrosine, phenylalanine, histidine, lysine, arginin.

(13) Carbohydrates in hydrolyzate: When hydrolyzed in 1N HCl at 80~90° C. for 3 hours, followed by the removal of the amino acids from the hydrolyzate by ion-exchange and further by hydrogenation of the hydrolyzate free from amino acids, the hydrogenated hydrolyzate contains the following carbohydrates: fructose, mannose, galactose, fucose, galactosamine, glucosamine.

Judging from the above-mentioned properties of the sample substance, it is believed that the substance according to this invention consists essentially of a water-soluble, relatively low molecular weight glycoprotein. As a result of our careful examination of all these properties of the substance of this invention in comparison with those properties of known antitumor substances derived from shellfish given in literature including typically Japanese Patent Publication No. 8088/82, Japanese Patent KOKAI Nos. 41314/79 and 41315/79, U.S. patent application Ser. No. 404,971 and Journal of National Cancer Institute, 60, 6, 1499-1500 (1978), we believe that the substance according to this invention is not identical with any of those disclosed in literature but novel and useful as antitumor agent.

The glycoprotein substance according to this invention can be derived from scallop. To be concrete, this substance may be prepared starting from the liquid portion to be discarded as waste which comes from cooking of raw scallop with a hot aqueous solvent or with the vapour of such solvent. The liquid portion which includes a condensate obtained in the cooking of raw scallop may be used as it is or in a concentrate or a dry powder derived therefrom. The isolation of the substance from the said liquid portion and the purification of the substance thus isolated may be effected in a manner known per se, that is by applying any one of or any combination of two or more of known means usually used for the isolation and purification of protein and carbohydrate substances in the art, such as, for example, centrifugation, dialysis, ultrafiltration, gel-filtration chromatography, ion exchange chromatography, chromatofocusing, ion exchange resin-treatment, affinity chromatography, liquid chromatography, electrophoresis, isoelectric focusing, salting-out, precipitation with organic solvent, isoelectric point-precipitation, vacuum-concentration, hot air-drying and freeze-drying. The sequence of two or more steps to be adopted for the isolation and purification of the object substance may be arranged as desired and repetition of certain treatment(s) may be done, if necessary.

According to one aspect of this invention, there is provided a process for the preparation of a glycoprotein substance possessing an antitumor activity from scallop which comprises recovering the liquid portion which comes from cooking of raw scallop with a hot aqueous solvent or with vapor of such solvent and which is to be discarded as waste, concentrating the liquid portion thus recovered to a smaller volume or to dryness to yield a concentrate or dry powder, dissolving the concentrate or dry powder in water to form an aqueous solution thereof and subjecting the aqueous solution to a series of treatments comprising ion exchange chromatography with a basic anion exchanger, isoelectric focusing and molecular weight-fractionating treatments (i.e. fractionating treatments to isolate a fraction of aimed molecular weight range) comprising gel-filtration and electrophoresis, in any desired sequence, whereby isolating a fraction consisting essentially of a glycoprotein substance which is adsorbable on a basic anion exchanger and which has an isoelectric point of pH 5.2 and an average molecular weight of about 5000.

A prepared embodiment of the process for the preparation of glycoprotein substance possessing an antitumor activity from scallop according to this invention comprises the steps of recovering the liquid portion which comes from cooking of raw scallop with a hot aqueous solvent or with vapor of such solvent and which is to be discarded as waste, concentrating the liquid portion thus recovered to a smaller volume or to dryness to yield a concentrate or dry powder, dissolving the concentrate or dry powder in water to form an aqueous solution thereof, subjecting the aqueous solution to ion-exchange chromatography with a basic anion exchanger to isolate a fraction which is adsorbed on the basic anion exchanger, subjecting the fraction to isoelectric focusing to isolate a fraction comprising substances having an isoelectric point of pH 5.2 and subjecting the resulting fraction to a series of molecular weight-fractionating treatments comprising gel-filtration and electrophoresis whereby to isolate a fraction having an average molecular weight of about 5000.

The liquid portion coming from cooking of raw scallop shellfish to be used as starting material according to the process of this invention may include those by-produced when fresh or raw scallop which may have been heated, if desired, is cooked or heat-treated in a hot aqueous solvent or with vapor of such solvent for the purpose of obtaining edible portions thereof. The hot aqueous solvent to be used as heating medium may include hot or boiling water, steam and other hot aqueous solvents such as saline solution and sea water and vapor of such solvents.

In order to take up edible portion of scallop shellfish and to recover the liquid portion containing antitumor substances by cooking or heat-treating (hereinafter referred to as "cooking") raw scallop in a hot aqueous solvent or with vapor of such solvent, the cooking operation is effected in one or more steps, in each of which the scallop is brought into contact with a hot aqueous solvent in the form of liquid and/or vapor which serves as both heating medium and extracting solvent. The method of contact between scallop and hot aqueous solvent may be selected as desired, for example from among those of direct exposure to solvent vapor, direct pouring of hot solvent and immersion into hot solvent. The hot aqueous solvent may be used in the form of either liquid or vapor or both.

For the purpose of this invention, the raw scallop may be used in its entirety, i.e. in the shell, or a shelled form with or without liver, as desired. According to this invention, therefore, all the edible portions, i.e. meat, ligament and the like, of scallop can be used for food after the cooking operation because no cutting or grinding of shellfish is required for cooking.

Usually, the cooking may be carried out at a temperature of about $50 \sim 120°$ C., preferably about $60 \sim 120°$ C. for a period of time of about $3 \sim 120$ minutes, preferably about $5 \sim 60$ minutes.

The liquid portion coming from the cooking of raw scallop shellfish as above-mentioned, which contains antitumor substances, may be concentrated to a smaller volume or to dryness to yield a concentrate or dry powder in a known manner, e.g. by heating in vacuo, hot air-drying or freeze-drying. Hot air-drying such as one using a spray drier is preferred in order to prevent or minimize the deterioration of the object substances because the contact (residence) time is as short as about $5 \sim 80$ seconds under conditions of the hot air temperature of about $200 \sim 350°$ C. at the inlet and of about $80 \sim 170°$ C. at the outlet.

The isolation of the glycoprotein substance of this invention from the concentrate or dry powder thus obtained and the subsequent purification may be carried out, according to one embodiment of this invention, as follows:

The concentrate or dry powder is dissolved in an aqueous solvent and the solution is centrifuged or filtered to remove insoluble matters and then desalted by gel-filtration or dialysis, for example. The resulting solution is subjected to ion-exchange chromatography with a basic anion exchanger such as an ion-exchanging gel having such dissociating group as diethylaminoethyl group or animoethyl group with the elution of the adsorbed fraction being effected with aqueous NaCl solutions (about $0.07 \sim 0.4$ mol/l) as eluents. The eluted fractions are subjected to isoelectric focusing under conditions capable of collecting a fraction or fractions having an isoelectric point of pH 5.2, for example under a pH range of $4.7 \sim 5.4$. The fraction or fractions so collected are then subjected to molecular weight-fractionating treatment such as vertical slab gel-electrophoresis and gel-filtration to obtain the object substance having an average molecular weight of about 5000. Optional step or steps for the purposes of desalting and concentration may be inserted at any suitable point between steps involved in the process, if desired. The desalting may be effected typically by dialysis or gel-filtration and the concentration may be carried out typically by heating in vacuo or freeze-drying.

The water-soluble glycoprotein substance according to this invention is useful as antitumor agent with such particular advantages that it has a broad antitumor spectrum without appreciable cytotoxicity and that a noticeable tumor regression effect can be achieved by adopting various administration routes which are normally applied in the management of cancers. Thus, intratumor, subcutaneous, intraperitoneal, intracutaneous, intramuscular, or intravenous injections, if necessary, oral and rectal administrations, or in external applications, coating, instillation and other methods of administration are feasible.

The process of this invention is also advantageous in view of environmental protection in that a substantial amount of organic substances contained in the liquid portion coming from cooking of raw scallop can be recovered as useful product with the result that the organic contents of the waste liquor are substantially reduced.

In the tests hereinafter given, the evaluation of antitumor activity of the antitumor substances isolated was made by the following method unless otherwise stated.

Four millions of Sarcoma 180 cells are subcutaneously transplanted into the right inguinal region of female ICR mice, 6 weeks old. Then, the test samples dissolved or suspended in a physiological saline in adequate concentrations (injection volume, 0.1 ml) are subcutaneously injected into the left inguinal region of the mice under test three times every second day. Three weeks after the tumor cell transplantation, the diameter of growing solid tumor or the weight of solid tumor removed is measured and the data obtained are compared with those of control group wherein a physiological saline solution is used in place of the test sample solution.

The inhibition ratios and complete tumor regression are calculated by the following formula:

$$\text{Inhibition ratio (\%)} = \left(1 - \frac{\text{Average tumor weight of the treated group}}{\text{Average tumor weight of the control group}}\right) \times 100$$

$$\text{Complete tumor regression} = \frac{\text{The number of mice showing complete tumor regression}}{\text{The total number of mice tested}}$$

This invention is now illustrated with reference to the following Examples to which the invention is in no way limited.

Example 1

One part (by weight) of raw scallop shellfish (*Patinopecten yessoensis*) in the shells was charged into a vessel continuously, into which 0.10 parts (by weight) of superheated steam at 105~110° C. was blown so that the raw scallop shellfish was directly exposed to the blown steam and cooked at 90~100° C. for 10 minutes. At the bottom of the vessel, there was collected a volume of the water condensate containing the active substances dissolved therein as a first crop solution of the active substances. The outer shells of raw scallop shellfish used as the starting material had about 0.1 parts (by weight) of the infesting acorn shells attached thereto. The first crop solution of the active substances was removed out of said vessel and then slowly cooled down from 90° C. to 50° C. and then immediately passed through a spraying drier. This drier had an inlet through which a stream of hot air at 280° C. was passed into the drier, as well as an outlet through which the effluent gases were discharged from the drier at a temperature of 125° C. The first crop solution of the active substances was dried in the drier in a retention time of 45 seconds to give a first crude powder of the active substances (Sample 1a) in a yield of 0.27% by weight based on the raw scallop shellfish employed.

Then, the ligament portions were removed from the scallop by means of knife. The scallop ligament so collected (50 kg) was placed into a volume (450 kg) of a boiling saline solution containing 10% by weight of sodium chloride in water, boiled in the boiling saline solution for 20 minutes and then removed therefrom. With the same saline solution, further three 50 kg portions of the scallop ligament were treated in the same manner as above. This saline solution was recovered as a second crop solution of the active substances. The second crop solution of the active substance was slowly cooled down from 90° C. to 40° C. and dried in the same manner as that for the first crop solution of the active substances to give a second crude powder of the active substances (Sample 1b) in a yield of 0.20% by weight based on the scallop shellfish employed.

Two parts by weight of the first crude powder were mixed with one part by weight of the second crude power to give a third crude powder of the active substances (Sample 1c).

Example 2

This third crude powder, i.e. Sample 1c, (600 g) obtained in Example 1 was dissolved in 3 l of 0.1 M phosphate buffer solution (pH 7.5) and the resulting solution was centrifuged at 10,000 G for 20 minutes to remove the insoluble deposits therefrom. The solution obtained was charged for the desalting purpose into a column (15 cm in height and 16 l in volume) of Sephadex G-25 (a product of Pharmacia Fine Chemicals Co., which is a gel for gel-filtration obtained by three-dimensionally crosslinking dextran with epichlorohydrin and which is capable of fractionating substances of molecular weights in the range of about 500~5000) which had been well equilibrated with the same phosphate buffer solution as that used above. A gel-filtration chromatography for the desalting purpose was effected by passing as developer a further amount of the same phosphate buffer solution as that used above through the column at a flow rate of 20 l/hr. By the term "a phosphate buffer solution" used herein is meant an aqueous solution of a phosphate mixture of potassium dihydrogenphosphate and disodium hydrogenphosphate. The electroconductivity of the eluate was measured continuously whereby to separate fractions containing lower molecular weight substances such as inorganic salts and fractions containing higher molecular weight substances. The desalted eluate fractions were then passed through a column of 16 l packed with an ion-exchanging gel, DEAE-Sepharose CL-6B (a product of Pharmacia Fine Chemicals, Co. which is a gel obtained by three-dimensionally crosslinking agarose with 2,3-dibromopropanol followed by introducing diethylaminoethyl group through an ether linkage and which has chlorine ion as counter ion, the upper limit of molecular weights to be fractionated of about $1 \times 10^6$ and the total exchange capacity of $15 \pm 2$ meq/100 ml) which had been well equilibrated with the same phosphate buffer solution as that used above to remove non-adsorptive substances. The column was well washed with the same phosphate buffer solution as that used above and then eluted with an eluent which was a mixture of the same phosphate buffer solution as that used above with 0.2 M sodium chloride solution. The eluted fractions containing glycoprotein substances of different molecular weights were collected and concentrated in vacuo below 30° C. to a volume of 2 l which was about one-fifths of the initial volume. The concentrate was dialyzed against distilled water for 48 hours for desalting and then freeze-dried to yield 6.08 g of a glycoprotein powder (S).

In order to examine the entity of the active substance or substances in the powder (S) so obtained, the power (S) was first subjected to isoelectric focusing (hereinafter referred to as Test A) as follows:

A gel bed containing 500 mg of the powder (S) was prepared for the purpose of isoelectric focusing over the range of from pH 4.0 to pH 6.0 by pouring into a mold (10.9 cm in width, 24 cm in length and 5.5 mm in thickness) 100 ml of Sephadex G 100 superfine gel containing 2% by weight of Servalyt AG 4-6 and 500 mg of powder (S) and slowly drying the contents of the mold to form about 70 g of a gel. Sephadex G 100 superfine is a product of Pharmacia Fine Chemicals Co., which is obtained by three-dimensionally crosslinking dextran with epichlorohydrin and which is capable of fractionating substances having molecular weights ranging about 2000~100,000 and was used as carrier and Servalyt AG 4-6 is a product of Serva AG, which is a mixture of amphoteric electrolytes comprising aliphatic compounds having molecular weights ranging 500~800 and containing secondary and tertiary nitrogen-containing groups such as guanid group, sulfonic acid group and phosphonic acid group and was used as carrier ampholyte to give a pH gradient of 4.0~6.0. Isoelectric focusing was effected using the gel bed so produced under the conditions of constant power of 20 W for 10 hours to fractionate the substances into three fractions, namely fraction (A) with pH values lower than 4.7, fraction (B) with pH values of 4.7~5.4 and fraction (C) with pH values higher than 5.4. Respective gel portions containing respective fractions (A), (B) and (C) were cut off and filtered using sufficient amount of distilled water to remove the carrier gels, yielding solutions containing respective fractions. Each of the eluate solutions was freeze-dried to give dry powder which was then dissolved in a small volume of distilled water for gel-filtration chromatography to remove the carrier ampholyte used. The solution was charged into a column of Sephadex G 50 (a product of Pharmacia Fine Chemicals Co. which is a gel obtained by three-dimensionally crosslinking dextran with epichlorohydrin and which is capable of fractionating substances having molecular weights ranging about 500~30,000) which had been well equilibrated with distilled water, whereby to remove fractions of substances having molecular weights lower than 2500 from each of fractions (A), (B) and (C), yielding fractions of substances having molecular weights not lower than 2500 to give glycoprotein powders (A-1), (B-1) and (C-1) after freeze-drying, respectively. The yield and antitumor activity according to the test method above-mentioned of each of the powders obtained are shown in Table 1.

TABLE 1

| Sample | Yield (mg) | Dose (mg/mouse × times)* | Average weight of tumors (g) | Inhibition ratio (%) | Complete regression |
|---|---|---|---|---|---|
| Control | — | — | 1.85 | — | 0/9 |
| B-1 | 165 | 1 × 3 | 0.17 | 90.8 | 1/8 |
| A-1 | 269 | 1 × 3 | 0.42 | 77.3 | 0/8 |
| C-1 | 274 | 1 × 3 | 0.65 | 64.9 | 0/9 |

*Subcutaneously injected into groin 1, 3 and 5 days after the transplantation of tumor cells; and evaluated 3 weeks after the transplantation.

It is seen from the bioassay results above that all the fractions (A-1), (B-1) and (C-1) contain antitumor substances and that the fraction (B-1), i.e. the fraction having isoelectric point-pH range of from 4.7 to 5.4, contains a substance possessing the highest antitumor activity.

Then, the fraction (B-1) was subjected to SDS-5% polyacrylamide gel-electrophoresis (hereinafter referred to as Test B) to examine the molecular weight distribution of the fraction. SDS-polyacrylamide gel-electrophoresis is electrophoresis using a gel prepared by polymerizing a liquid mixture comprising acrylamide monomer, N,N'-methylenebisacrylamide as crosslinking agent, a polymerization catalyst and sodium dodecyl sulfate (SDS). "5% polyacrylamide" in the electrophoresis means the concentration of acrylamide in the iqud mixture being 5% by weight. The electrophoresis of the fraction B-1 showed a peak of single band with strong color development at a position of relatively low molecular weight which seemed to be around 5000 and a continuous color development over a range of molecular weights of about 10,000 to 300,000. Having taken particular attention to the existence of such low molecular weight substance showing a single band as above, we intended to isolate this substance and to examine the antitumor activity thereof. The isolation of this substance was carried out as follows:

Three portions of 20 mg of the fraction (B-1) were subjected to vertical slab gel-electrophoresis at pH 8.0 according to 7.5% polyacrylamide gel-electrophoresis. The gel used was prepared by polymerizing a liquid mixture comprising acrylamide, N,N'-methylenebisacrylamide and a polymerization catalyst in a mold (14 cm × 14 cm × 2 mm, 40 ml in volume). Thus, there were separated a low molecular weight fraction with Rf values higher than 0.93 which corresponds to molecular weight of 5500 and a high molecular weight fraction with Rf values of 0~0.93 in relation to Rf of Bromophenol blue. The gel containing the low molecular weight fraction was finely divided in a homogenizer containing 0.1 M phosphate buffer solution at pH 7.5 and extracted in the buffer solution. The extract was freeze-dried to give a dry powder, which was then desalted in such manner that the powder was dissolved in 10 ml of distilled water and the solution was passed through a column of Sephadex G 25 with the subsequent elution with distilled water whereby to collect fractions free from substances having molecular weight lower than 2000 such as inorganic salts and the fractions so collected were freeze-dried to give 12 mg of a dry powder (Sample B-1-a). By way of reference, the gel containing the high molecular weight fraction with Rf values of 0~0.93 was treated in the same manner as that used for treatment of the gel containing the low molecular weight fraction whereby to give 36 mg of a dry powder (Sample B-1-b).

The two powders thus obtained were evaluated on the antitumor activities thereof by the method referred to above with the results given in Table 2.

TABLE 2

| Sample | Dose (mg/mouse × times)* | Average weight of tumors (g) | Inhibition ratio (%) | Complete regression |
|---|---|---|---|---|
| Control | — | 2.05 | — | 0/7 |
| B-1-a | 0.2 × 3 | 0.22 | 89.3 | 1/5 |
| B-1-b | 0.2 × 3 | 0.64 | 67.8 | 0/5 |

Sample (B-1-a) corresponds to the fraction of molecular weight of about 5500 or lower (actual molecular weight being about 5000 as shown in Examples hereinafter shown) in slab gel-electrophoresis of the fraction (B-1) collected at isoelectric point pH range of 4.7~5.4 in isoelectric focusing of Sample (S).

It is surprising that Sample (B-1-a) contains a substance possessing a significantly higher antitumor activity than that of Sample (B-1-b) containing all substances with molecular weights higher than 5500 as given in Table 2.

Example 3

For the purpose of fractionating the powder (S) obtained in Example 2 by preparatory isoelectric focusing, three gel beds which can be used at isoelectric point pH range of 4.0~6.0 were prepared in the same manner as that described in Test A of Example 2 using a gel prepared by suspending and swelling in distilled water Sample (S) (1.5 g) together with Sephadex G-100 Superfine gel (a product of Pharmacia Fine Chemicals Co.) and Servalyt AG4-6 (a product of Serva AG), well washing the mixture with distilled water, filtering the gel mixture and drying it to give powdery gel.

Each of the gel beds containing Sample (S) was subjected to isoelectric focusing under conditions of constant power of 20 W for 14 hours to fractionate the gel into fraction (D) with pH values of 5.0 and lower, fraction (E) with pH values higher than 5.0 and lower than 5.4 and fraction (F) with pH values of 5.4 and higher. Fraction (F) was discarded and fraction (D) and fraction (E) each were washed with sufficient amount of distilled water to separate into gel and filtrate, respectively. Respective filtrates derived from fraction (D) and fraction (E) were freeze-dried to give respective powders, each of which was dissolved in a small amount (10 ml) of distilled water and the solution was subjected to gel-filtration chromatography with Sephadex G-50 gel to separate a fraction having molecular weights higher than 2500 in the same manner as that used in Test A of Example 2. Thus, there were obtained a fraction with molecular weights higher than 2500 and pH of lower than 5.0 as fraction (D-1) and a fraction with molecular weights higher than 2500 and pH of 5.0~5.4 as fraction (E-1), which were freeze-dried to give 26 mg of powder (D-1) and 59 mg of powder (E-1), respectively.

A portion of both powder (D-1) and powder (E-1) was subjected to SDS-20% polyacrylamide gel-electrophoresis under conditions of a constant current of 50 mA for 6 hours and the molecular weights of the migrated substances were measured in compared with standard substances such as insulin A, insulin B, cytochrome C, chymotrypsinogen A and ovalbumin according to conventional method. The result was that powder (D-1) contained little or no substances with color development at Rf value corresponding to molecular weights of 4000~5000, whereas powder (E-1) showed a strong color development in a single band at Rf value corresponding to molecular weights of 4000~5000, revealing that the substance having average molecular weight of 5000 and possessing the highest antitumor activity as shown in Test B of Example 2 was contained in powder (E-1). Further, there was shown by the result that both powder (D-1) and powder (E-1) showed a number of bands corresponding to molecular weights higher than 10,000, but no peak corresponding to molecular weights between 5000 and 10,000.

Powder (E-1) was further fractionated with the intention of isolating the substance of average molecular weight of about 5000 and with the highest antitumor activity as follows:

Twenty (20) mg of powder (E-1) was dissolved in 2 ml of distilled water and the solution was subjected to electrophoresis at a constant current of 50 mA for 3 hours in a vertical slab gel of 7.5% polyacrylamide (14 cm in width and 2 mm in thickness) using a phosphate buffer solution at pH 8.0. This operation was repeated two times, after which the gel was divided, depending on Rf values determined in relation to that of Bromophenol blue, into two portions, that is a lower molecular weight fraction with Rf values of 0.93 and higher (i.e. fraction containing a glycoprotein substance having average molecular weight of about 5000 according to this invention) and a higher molecular weight fraction with Rf values lower than 0.93 (i.e. fraction containing glycoprotein substances having average molecular weight higher than about 5000). The former gel fraction was stirred in a homogenizer containing 0.1 M phosphate buffer solution at pH 7.5 to peptize the gel and then filtered to separate the gel and filtrate having the substance with Rf values of 0.93 and higher extracted and the filtrate was freeze-dried to give a powder. The powder was then dissolved in 10 ml of distilled water and the solution was desalted by gel-filtration chromatography using a column (1 cm in inner diameter and 45 cm in height) of Sephadex G-25 with distilled water as eluent whereby to collect fractions of molecular weights higher than 2500 free from inorganic salts and the fractions were freeze-dried to give 14 mg of a powder hereinafter referred to as powder (F).

Example 4

The average molecular weight of powder (F) obtained in Example 3 was measured by SDS-20% polyacrylamide vertical gel-electrophoresis relatively to molecular weight-reference standard substances such as insulin A, insulin B, cytochrome C, chymotripsinogen A, ovalbumin and tryptophane. As a result, powder (F) revealed a single peak band at the position corresponding to average molecular weight of 5000 (with tolerance of about ±1000).

The isoelectric point of powder (F) was also measured by isoelectric focusing over pH range of 4.0~6.0 using Servalyt Precotes 4-6 (a product of Serva AG which is a gel comprising Servalyt AG 4-6 and 5% polyacrylamide gel) as precoated film for isoelectric focusing. As a result, powder (F) showed a single peak band at about pH 5.2.

Physico-chemical properties of powder (F) were also measured, which are as shown hereinbefore.

Example 5

Sarcoma 180 tumor cells (about $6 \times 10^6$ cells) were subcutaneously transplanted into the right groin of female ICR mice, 6 weeks old. The test samples of powder (F) obtained in Example 3 which were dissolved in a physiological saline in appropriate concentrations (injection volume: 0.1 ml) with pH 7.0 were injected on 5th, 7th and 9th days after the tumor cell transplantation. The injections were effected through several routes, namely directly into the tumor site, intravenously into the tail, intraperitoneally and subcutaneously into the opposite groin. After the lapse of 5 weeks from the transplantation, the mice were killed and the solid tumors were dissected out and weighed. The results were compared with those of control group wherein a physiological saline solution was administered in place of each test sample. Inhibition ratio (%) and complete regression were calculated as defined hereinbefore. The results are shown in Table 3.

TABLE 3

| Administration route | Dose (mg/mouse × times) | Average weight of tumors (g) | Inhibition ratio (%) | Complete regression |
|---|---|---|---|---|
| Control | — | 8.63 | — | 0/8 |
| Directly into | 0.2 × 3 | 1.52 | 82.4 | 1/5 |
| tumor site | 0.1 × 3 | 1.83 | 78.8 | 2/5 |
| Intravenously | 0.2 × 3 | 0.83 | 90.4 | 2/4 |
| into tail | 0.1 × 3 | 0.43 | 95.0 | 3/4 |
| Intraperitoneally | 0.2 × 3 | 2.50 | 71.0 | 2/5 |
| Subcutaneously | 0.2 × 3 | 0.87 | 89.9 | 2/5 |
| into groin | 0.1 × 3 | 0.69 | 92.0 | 2/5 |

The results given in Table 3 demonstrate that powder (F) isolated in Example 3 are remarkably effective in degeneration and complete regression of Sarcoma 180 solid tumors through various routes for administration, that is in tumor site, intravenously, intraperitoneally and subcutaneously.

Direct cytotoxicity of powder (F) was also examined against L 5178 Y Lymphoma cells on mice, but there was found no appreciable cytotoxicity.

The test on cytotoxicity was effected as follows:

Leukemia cells (about $5 \times 10^5$ cells/ml) of L 5178 Y were suspended in a tissue culture medium, Eagle MEM (containing 15% calf serum) and the suspension, after the addition of test sample in the concentration as undermentioned thereto, was incubated in an incubator under 5% $CO_2$ in air at 37° C. for 48 hours. Then the effect of test sample on target cell proliferation was estimated with a phase-contrast microscope. A physiological saline solution and mitomycin C were used as control and reference, respectively. The results of the direct cytotoxicity test are shown in Table 4.

TABLE 4

| Sample | Concentration of sample (μg/ml) | Growth inhibition (%) |
|---|---|---|
| Powder (F) of this invention | 40 | 0 |
|  | 200 | 0 |
| Mitomycin C | 20 | 25 |
|  | 100 | 65 |
| Control (Physiological saline solution) |  | 0 |

Example 6

This Example illustrates the antitumor activity of powder (F) isolated in Example 3 on several solid tumors other than Sarcoma 180 solid tumor.

The tumor cells ($4 \times 10^6$ cells) of each of Ehrlich carcinoma, Leukemia SN-36, NTF reticulum cell sarcoma and methylcholanthrene-induced Fibrosarcoma which were maintained in ICR female mice or Balb/c mice (for Fibrosarcoma only) were subcutaneously transplanted into one groin of another group of female, 6 weeks aged ICR mice or Balb/c mice, correspondingly. One week after the transplantation, the tumor cells were confirmed to have grown to solid tumors. Then, a solution in physiological saline of powder (F) was directly injected into the tumor site at a dose of 0.2 mg/mouse three times on alternate days. Five weeks after the tumor cell transplantation, the solid tumors were dissected out and weighed. The results were compared with those of control group wherein a physiological saline solution was administered in place of each test solution. Inhibition ratio (%) and complete regression were calculated as hereinbefore defined. The results are shown in Table 5.

TABLE 5

|  | Ehrlich carcinoma | SN-36 | NTF | Fibrosarcoma |
|---|---|---|---|---|
| Inhibition ratio (%) | 95.3 | 100 | 100 | 100 |
| Complete regression | 3/4 | 3/3 | 4/4 | 4/4 |

Example 7

The procedures described in Examples 2 and 3 were repeated except that Sample 1a was used in place of Sample 1c, yielding an antitumor substance consisting essentially of a water-soluble glycoprotein substance having average molecular weight of 5000. The physico-chemical properties and antitumor activity of this substance were substantially the same as those of powder (F) isolated in Example 3.

Example 8

The procedures described in Examples 2 and 3 were repeated except that Sample 1b was used in place of Sample 1c, yielding an antitumor substance consisting essentially of a water-soluble glycoprotein substance having average molecular weight of 5000. No difference could be found between the physico-chemical properties and antitumor activity of this substance and those of powder (F) isolated in Example 3.

What we claim is:

1. A glycoprotein substance possessing an antitumor activity which is recovered from the liquid portion coming from cooking of raw scallop shellfish with a hot aqueous solvent or with the vapor of such solvent and which has the following characteristics:

(1) Appearance: White, powdery solid;
   (2) Solubility: Soluble in water, but insoluble in organic solvents such as methanol, ethanol and acetone;
   (3) Acidic or basic nature: Amphoteric electrolyte having an isoelectric point of pH 5.2;
   (4) Infrared absorption spectrum (pelleted in KBr): With characteristic absorption peaks at $3500 \sim 3300$, 1660 and 1550 cm$^{-1}$;
   (5) Ultraviolet absorption spectrum in an aqueous solution: With a characteristic absorption peak $\lambda_{max}^{H2O}$ at 279 nm;
   (6) Color reactions: Positive in biuret reaction, xanthoproteic reaction, phenolic reagent reaction according to Lowry-Folin method, anthrone-sulfuric acid reaction and phenol-sulfuric acid reaction, but negative in cysteine-sulfuric acid reaction;
   (7) Average molecular weight: About 5000 as measured by gel-electrophoresis.

2. A glycoprotein substance possessing an antitumor activity which is recovered from the liquid portion coming from cooking of raw scallop shellfish with a hot aqueous solvent or with the vapor of such solvent by concentrating the liquid portion to a smaller volume or to dryness to give a concentrate or dry powder, dissolving the concentrate or dry powder in water to form an aqueous solution thereof, subjecting the aqueous solution to a series of treatments comprising ion-exchange chromatography with a basic anion exchanger, isoelectric focusing and molecular weight-fractionating treatments comprising gel-filtration and electrophoresis, in any desired sequence, and which has the following characteristics:

(1) Appearance: White, powdery solid;
   (2) Solubility: Soluble in water, but insoluble in organic solvents such as methanol, ethanol and acetone;
   (3) Acidic or basic nature: Amphoteric electrolyte having an isoelectric point of pH 5.2;
   (4) Infrared absorption spectrum (pelleted in KBr): With characteristic absorption peaks at $3500 \sim 3300$, 1660 and 1550 cm$^{-1}$;
   (5) Ultraviolet absorption spectrum in an aqueous solution: With a characteristic absorption peak $\lambda_{max}^{H2O}$ at 279 nm;
   (6) Color reactions: Positive in biuret reaction, xanthoproteic reaction, phenolic reagent reaction according to Lowry-Folin method, anthrone-sulfuric acid reaction and phenol-sulfuric acid reaction, but negative in cysteine-sulfuric acid reaction;
   (7) Average molecular weight: About 5000 as measured by gel-electrophoresis.

3. A process for the preparation of a glycoprotein substance having an average molecular weight of about 5000 and an isoelectric point of pH 5.2 from scallop shellfish which comprises recovering the liquid portion which comes from cooking of raw scallop shellfish with a hot aqueous solvent or with vapor of such solvent and which is to be discarded as waste, concentrating the liquid portion to a smaller volume or to dryness to yield a concentrate or dry powder, dissolving the concentrate or dry powder in water to form an aqueous solution thereof, subjecting the aqueous solution to a series of treatments comprising ion-exchange chromatography with a basic anion exchanger, isoelectric focusing and molecular weight-fractionating treatments comprising gel-filtration and electrophoresis, in any desired sequence, whereby to isolate a glycoprotein substance which is adsorbable on the basic ion exchanger and which has an average molecular weight of about 5000 and an isoelectric point of pH 5.2.

4. A process according to claim 3 wherein after the concentrate or dry powder is dissolved in water, the aqueous solution so formed is subjected to ion-exchange chromatography with a basic anion exchanger to isolate a fraction adsorbed on the basic anion exchanger and the fraction is then subjected to isoelectric focusing to isolate a fraction containing substances having an isoelectric point of pH 5.2 and the fraction thus isolated is subjected to molecular weight-fractionating treatments comprising gel-filtration and electrophoresis to isolate a substance having an average molecular weight of about 5000.

* * * * *